United States Patent [19]

Murray, Jr. et al.

[11] Patent Number: 4,752,115
[45] Date of Patent: Jun. 21, 1988

[54] OPTICAL SENSOR FOR MONITORING THE PARTIAL PRESSURE OF OXYGEN

[75] Inventors: Richard C. Murray, Jr., Palatine; Steven M. Lefkowitz, Hoffman Estates, both of Ill.

[73] Assignee: Spectramed, Inc., Newport Beach, Calif.

[21] Appl. No.: 699,515

[22] Filed: Feb. 7, 1985

[51] Int. Cl.$^4$ .................... G02B 6/16; G01N 33/48
[52] U.S. Cl. ............................. 350/96.29; 350/96.34; 356/41
[58] Field of Search ............ 250/357.1, 361 C, 361 R, 250/362, 458.1, 459.1, 483.1, 484.1, 485.1, 486.1, 487.1; 350/96.29, 96.30, 96.31, 96.33, 96.34; 356/41

[56] References Cited

U.S. PATENT DOCUMENTS

| | | | |
|---|---|---|---|
| 4,003,707 | 1/1977 | Lubbers et al. | 23/232 |
| 4,041,932 | 8/1977 | Fostick | 128/2 |
| 4,306,877 | 12/1981 | Lubbers | 23/230 |
| 4,321,057 | 3/1982 | Buckles | 23/230 |
| 4,399,099 | 8/1983 | Buckles | 422/58 |
| 4,476,870 | 10/1984 | Peterson et al. | 356/41 X |
| 4,587,101 | 5/1986 | Marsoner et al. | 250/462.1 X |

OTHER PUBLICATIONS

Demas et al., "Energy Transfer from Luminescent Transition Metal Complexes to Oxygen", J. of Am. Chem. Soc., IC No. 11 (5/25/66), pp. 3547-3551.
Klassen et al., "Spectroscopic Studies of Ruthenium (II) Complexes . . . ", The Journal of Chemical Physics, XLVIII No. 4 (2/15/68) pp. 1853-1858.
Roswell et al., "Energy Transfer in Chemiluminescence", Journal of the American Chemical Society, XCII, No. 16 (8/12/70), pp. 4855-4860.
Eastwood et al., "Porphyrins", Journal of Molecular Spectroscopy, XXXV, (1970), pp. 359-375.
Peterson et al., "Fiber-Optic Probe for in Vivo Measurement of Oxygen Partial Pressure", Analytical Chemistry, LVI (1984), pp. 62-67.
"Fiber Optics Simplify Remote Analysis", C&EN, 9/27/82, pp. 28-30.
Fordyce et al., "Electronic Spectroscopy of Diphosphine- and Diarsine-Bridge . . . ", Journal of Am. Chem. Soc., CIV (1982), pp. 985-988.
Che et al., "Spectroscopic Properties and Redox Chemistry of Phosphorescent . . . ", Journal of Am. Chem. Soc., CIII (1981), pp. 7796-7797.
Norcea et al., "Electron-Transfer Chemistry of the Luminescent Excited State . . . ", Journal of the Am. Chem. Soc., CIII (1981), 9349-7350.
Demas et al., "Oxygen Quenching of Charge-Transfer Excited States of Ruthenium . . . ", Journal of the American Chemical Society, XCV No. 20 (10/3/73), pp. 6864-6865.

Primary Examiner—Eugene R. LaRoche
Assistant Examiner—Steven J. Mottola
Attorney, Agent, or Firm—Lyon & Lyon

[57] ABSTRACT

A device is described for sensing oxygen, particularly for use in medical applications. The device includes an optical waveguide and an oxygen sensing medium disposed on the waveguide. The sensing medium fluoresces in response to light from a light source such that the intensity of fluorescence is dependent on the partial pressure of oxygen in the environment. The sensing medium includes an oxygen sensitive fluorescent dye in a matrix consisting of a plasticized polymer.

25 Claims, 2 Drawing Sheets

OPTICAL SENSOR FOR MONITORING THE PARTIAL PRESSURE OF OXYGEN

BACKGROUND OF THE INVENTION

The invention relates generally to sensors for monitoring the partial pressure of oxygen in various environments and more specifically relates to fiber-optic devices for monitoring the partial pressure of oxygen in medical applications.

Various amperometric electrochemical methods exist for measuring the partial pressure of oxygen. However, these methods are generally unsatisfactory for in vivo applications due to severe and unpredictable drift related to difficulties associated with the fabrication of microsensors and with membrane contamination. As used in this context, membrane contamination refers to clogging or fouling of the membrane and is highly undesirable because it can cause such devices to produce incorrect readings for the partial pressure of oxygen.

An alternative to the use of electrochemical sensors for in vivo applications is the use of optically based oxygen sensors. Several oxygen-based sensor systems have been described previously. For example, U.S. Pat. No. 4,003,707 issued Jan. 18, 1977, to Lubbers describes the idea of using quenching by oxygen of the fluorescence of pyrene dibutyric acid dissolved in dimethyl formamide with the solution enclosed in a gas-permeable membrane.

One problem, however, with the device described in the patent to Lubbers is that such devices are difficult to fabricate as miniature devices for use in medical applications.

Another optical device is described in Peterson, *Analyt. Chem.*, 56, 62–67 (1984). Peterson describes the use of a two-fiber optical cable having a sensing tip consisting of perylene dibutyrate absorbed on a powdered polystyrene support and enclosed in a gas permeable membrane. The dye is excited by light sent down one of the fibers. The resulting fluorescence is detected with the other fiber. Quenching of the fluorescence of perylene dibutyrate by oxygen is again used in this method.

Another general type of optical device for monitoring the partial pressure of oxygen can be based on the use of ruthenium (II) complexes as luminescent sensors. The properties of such complexes are described in Klassen et al., "Spectroscopic Studes of Ruthenium (II) Complexes. Assignment of the Luminescence", *The Journal of Chemical Physics*, Vol. 48, No. 4, (1968), Pages 1853–1858, and in Demas et al., "Energy Transfer from Luminescent Transition Metal Complexes to Oxygen", *Journal of the American Chemical Society*, Vol. 99, No. 11, (1977), Pages 3547–3551.

The use of perylene dibutyrate or pyrene dibutyric acid mounted on a solid support, or in solution, and enclosed in a membrane is unsatisfactory because of the complexity of fabrication and the poor sensitivity of the dyes. The luminescence of these dyes change substantially less than twofold when the partial pressure of oxygen changes from 0 to 760 mm. Hg. These changes have been measured and found to be only about ten percent or less. The ruthenium complex is much more sensitive than the other two materials, but is very slow to respond when used in the unplasticized polyvinyl chloride (PVC) or silicone rubber systems described by Demas and Bacon.

U.S. Pat. Nos. 4,399,099 and 4,321,057 to Buckles describes an oxygen sensor made by coating an optical fiber core with a cladding material which interacts with oxygen thereby changing the amount of transmitted light. His method requires that both ends of the fiber be accessible so that effectively two fibers (i.e., two fiber ends) are required for a given sensor if used in a catheter application.

The use of two fibers and/or a remote light source appears to be a requirement for most optical sensing devices for monitoring the partial pressure of oxygen. This makes the use of such devices impractical in remote sensing applications where only a single fiber is available, and where that single fiber must serve as both an excitation source and a signal conduit, particularly where space constraints exist.

Therefore, a need exists to provide a miniaturized sensing system, for monitoring the partial pressure of oxygen, which is easily fabricated, is sufficiently responsive to small changes in the partial pressure of oxygen, can be operated using a single optical fiber in remote applications, and is not subject to the effects of membrane contamination such as deterioration of the accuracy of the sensor.

SUMMARY OF THE INVENTION

The subject invention is a very fast, very sensitive, single-fiber oxygen sensor designed for remote applications in constructed environments. The sensor described herein is particularly useful in multisensor systems for very small channels such as in arteries and in blood vessels, or in single-lumen medical catheters. The invention includes an optical waveguide to receive light transmitted from a light source. The invention also includes an oxygen-sensing medium disposed on the waveguide. The sensing medium fluoresces in response to light from the light source. The intensity of fluorescence of the sensing medium is dependent upon the partial pressure of oxygen present in the environment to be monitored. The sensing medium includes an oxygen sensitive fluorescent dye in a matrix consisting of a plasticized polymer.

An object of the invention is to provide a miniaturized oxygen sensor for medical applications.

Another object of the invention is to provide an oxygen sensor which is capable of responding to very small changes in the partial pressure of oxygen on the order of 1 to 5 mm Hg.

Another object of the invention is to provide an oxygen sensor which is easily fabricated and maintains its integrity during continued use.

Yet another object of the invention is to provide an oxygen sensor which is not susceptible to the effects of membrane contamination when used in medical applications.

These and other objects and advantages of the invention, as well as the details of an illustrative embodiment, will be more fully understood from the following description and the drawings.

DETAILED DESCRIPTION OF THE PREFERRED EMBODIMENT

As noted above, the subject invention is a very fast, very sensitive single-fiber sensor designed for remote applications in constricted environments. The sensor is very easy to construct and can be used either for gas or liquid-phase monitoring. The subject invention comprehends that numerous embodiments can be used with regard to both the materials used and the geometric design of the sensor.

Figure 1:
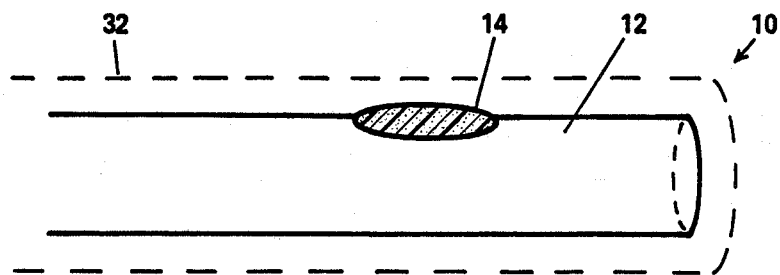
FIG. 1 is a schematic cross-sectional view illustrating one embodiment of the subject invention in which an oxygen sensing material is disposed along one side of an optical fiber.

FIG. 1 illustrates one embodiment of the sensor 10 in which a single optical fiber 12 having a core surrounded by a cladding is used. In this embodiment, a longitudinal portion of the cladding is removed to allow evanescent-wave light transmission from the core of the fiber to a sensing material 14. The sensing material and other aspects of this embodiment will be discussed in much greater detail below.

Figure 2:
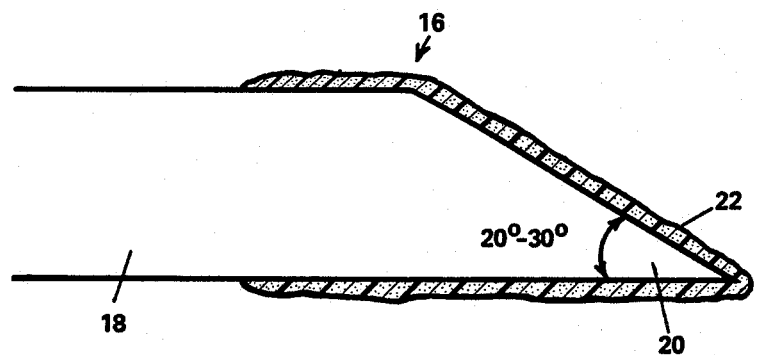
FIG. 2 is a schematic cross-sectional view illustrating another embodiment of the subject invention in which an oxygen-sensitive material is disposed about the tip of an optical fiber.

FIG. 2 illustrates another embodiment of the subject invention in which a sensor 16 includes a single optical fiber 18 which has a first end 20 which terminates in an acute angle to expose a portion of a core of the fiber 18. An oxygen-sensitive membrane 22 is applied to the first end of the fiber. In the preferred embodiment, the angle formed by the axis of light transmission through the fiber and the plane formed by the exposed portion of the core is thirty degrees. In other embodiments of the subject invention, the angle formed is generally less than sixty degrees. Experimental results indicate an angle which is substantially larger or smaller than twenty to thirty degrees tends to decrease the performance of the sensor. The performance is also affected by the smoothness of the exposed core surface.

Figure 3:
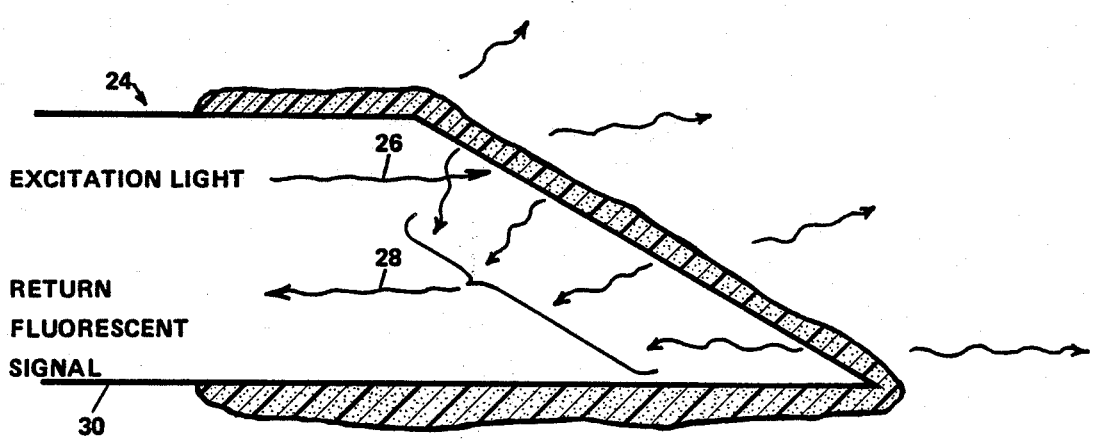
FIG. 3 is a schematic cross-sectional view illustrating the subject invention particularly showing the light transmitting and fluorescent characteristics of the subject invention.

FIG. 3 illustrates the light transmission characteristics and fluorescent characteristics of a typical sensor 24 fabricated in accordance with the subject invention. As can be seen from the figure, excitation light 26 and a fluorescent signal 28 both travel along the same optical fiber 30 so that extreme miniaturization or multiple sensors in a single small channel are possible. Experimental results, which will be discussed in further detail below indicate that a sensor fabricated in accordance with the subject invention has at least twice the sensitivity of any of the sensors described above in the Background of the Invention where sensitivity (S) is defined by the equation:

$$S = (I_0/I_{760} - 1)$$

where $I_0$ is the intensity of the fluorescent light at 0 mm Hg, and $I_{760}$ is the intensity of fluorescent light at 760 mm Hg. In addition, the subject invention has a much faster response time as will be discussed below. Another advantage of the subject invention over the prior art is that devices fabricated in accordance with the preferred embodiment provide a much larger absolute fluorescent signal than prior-art devices, thereby increasing the attainable precision.

In the preferred embodiment, a sensor is fabricated using a 250 micron diameter plastic optical fiber having first and second ends. The first end of the fiber is cut at an angle of twenty to thirty degrees from the fiber axis as illustrated in FIG. 2. As noted above, a steeper or shallower cut seems to decrease the performance of the sensor. The second end of the fiber is adapted to receive light from a light source and to provide an outlet for fluoresced light to go to a signal detector. In the preferred embodiment, the second end of the fiber is provided with a plastic optical connector ferrule. The area surrounding the second fiber end on the ferrule surface should be blackened so as not to reflect light from the excitation light source into the signal detector.

In the preferred embodiment, the first end of the fiber is dipped into a solution consisting of tris (4,7-diphenyl-1,10-phenanthroline) Ru(II) perchlorate, polyvinyl chloride (PVC) and plasticizer (usually didecyl phthalate) dissolved in tetrahydrofuran (or any other solvent for PVC and the plasticizer used which will not attack the fiber core or cladding). The optimum composition appears to be, by weight: 0.0254 gm tris (4,7-diphenyl-1,10-phenanthroline) Ru(II) perchlorate, 1.00 gm PVC, 1.00 gm didecyl phthalate, and 25 gms of tetrahydrofuran. Adding more solvent causes a thinner, faster-responding coating but produces a less intense signal; adding substantially less solvent causes a thicker, slower-responding, less sensitive coating. The plasticizer is necessary to produce the fast response and, to some extent, the high sensitivity; too much plasticizer decreases the mechanical stability of the sensing coating. The phthalate class of plasticizers (didecyl-, dicyclohexyl-, and ditridecyl-, for example) seems to perform best. In the optimum embodiment described above, the plasticized polymer includes fifty weight percent of didecyl phthalate. If a substantially lower percentage of plasticizer is used, the response time of the resulting sensor becomes excessively long; on the other hand, if a substantially higher percentage is used, the resulting polymer film is undesirably soft and easily removed.

In other embodiments, the plasticizer may be selected from a group of materials consisting of phthalic acid derivatives, citric acid derivatives, adipic acid derivatives, and sebacic acid derivatives. It is necessary that the plasticizer used be compatible with the specific polymer used in a particular embodiment. A plasticizer which is compatible with a specific polymer will produce a uniform, translucent film, whereas a plasticizer which is not compatible with a specific polymer will produce a grainy film which is generally opaque or will separate into two phases as the solvent evaporates.

As noted above, the preferred embodiment uses an oxygen sensitive fluorescent dye of tris (4,7-diphenyl-1,10-phenanthroline) Ru(II) perchlorate. In other embodiments, the oxygen sensitive dye may be made of any salt of the tris (4,7-diphenyl-1,10-phenanthroline) Ru(II) cation. In particular, the anion used can be taken from the group including thiocyanate, hexafluorophosphate, tetrafluoroborate, chloride or any of the other halides. In other embodiments, the oxygen-sensitive fluorescent dye is made of any salt of a transition-metal complex having as a ligand a derivative of 1,10-phenanthroline. In particular, the transition-metal cation should be taken from the group including ruthenium (II), osmium (II), rhodium (III) and iridium (III).

The subject invention envisions that various polymers may be used. For example, the polymer may be selected from the group of materials consisting of PVC, polystyrene, polyurethane, polyvinyl butyral, polymethyl methacrylate and silicone rubber. In general, any polymer may be used provided that the polymer can be plasticized to a high degree, that it is compatible with the dye used, and that it can be dissolved in a solvent which will not attack the optical fiber used.

In some embodiments it is desirable to provide a gas-permeable, solution-impermeable sleeve about the optical fiber or waveguide. This is illustrated in phantom in FIG.1 as element 32. In some embodiments the sleeve may be formed of polyethylene, polypropylene, or silicone rubber microbore tubing. The sleeve may be applied to the sensing device 10 by sliding a tube of the particular material used over the sensing device. In other embodiments, it is possible to apply the sleeve by coating the device with the material to be used and allowing the material to cure in place about the device.

Figure 4:
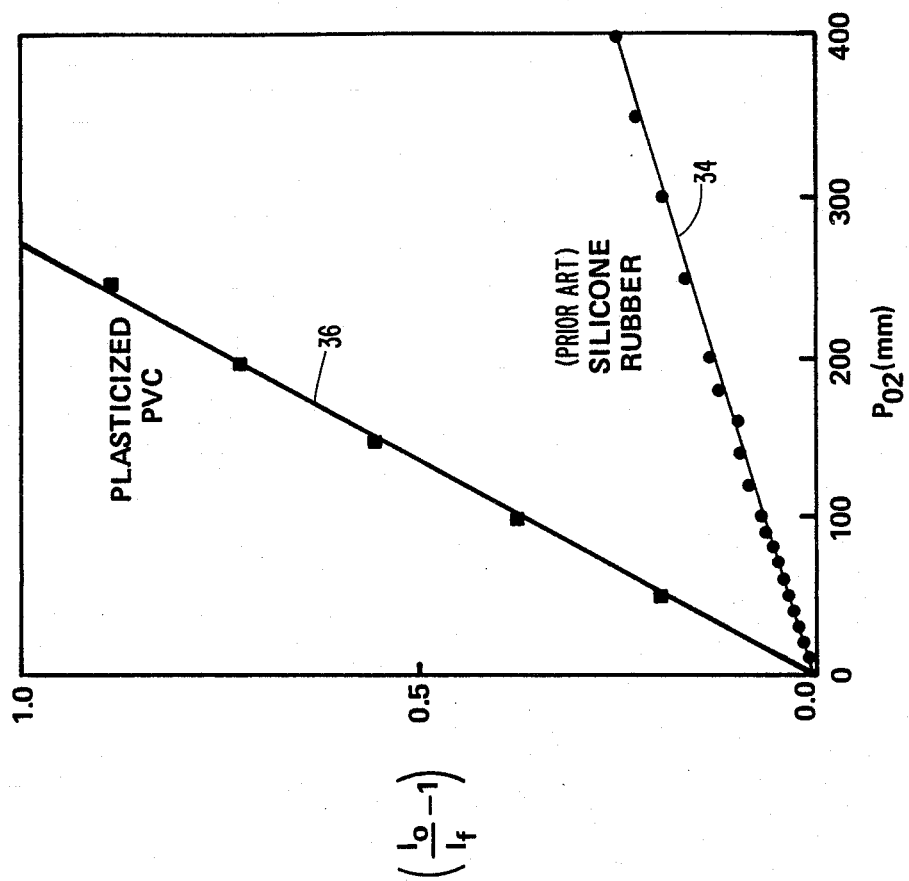
FIG. 4 is a Stern-Volmer plot showing the relative fluorescent intensity of light produced in a prior-art sensor and a sensor as described herein as a function of the partial pressure of oxygen.

FIG. 4 illustrates a Stern-Volmer plot showing the relative fluorescent intensity of light produced in a prior art sensor 34 and a sensor as described herein 36 as a function of the partial pressure of oxygen. A Stern-Volmer plot is a graph in which the fluorescence ratio of the sensor is plotted versus the percentage or partial pressure of oxygen. The fluorescence ratio (R) can be defined as:

$$R = (I_0/I_f - 1)$$

where $I_0$ is the fluorescence at zero oxygen partial pressure and $I_f$ is the fluorescence at a corresponding partial pressure of oxygen. As can be seen from the figure, the sensitivity of the device described herein is substantially greater than that of the prior-art sensor. The particular prior-art sensor that is used for comparison in FIG. 4 is a sensor of the type described above as developed by Demas and Bacon.

Figure 5:
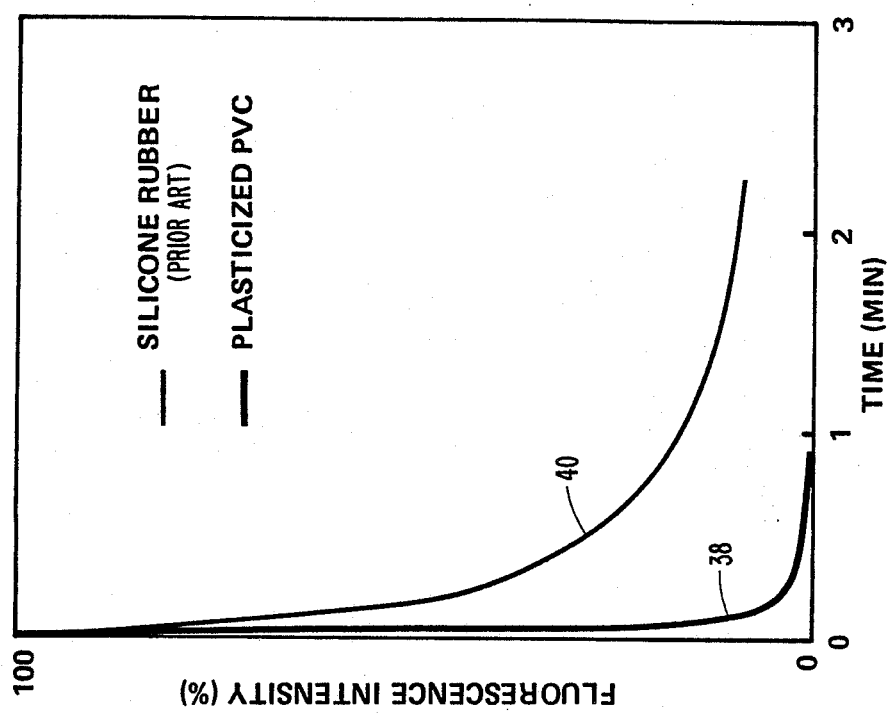
FIG. 5 is a graph illustrating the response times of a traditional sensor silicone rubber and a sensor of plasticized PVC as described herein.

Referring now to FIG. 5, the response time 38 of the device as described herein has proven to be substantially faster than the response time 40 of the prior art device as described by Demas and Bacon. These response times were monitored for a change in the partial pressure of oxygen from 0 to 760 mm Hg.

In summary, the present invention provides for the rapid, precise and accurate measurement of oxygen partial pressures in remote sensing applications due to the use of a very sensitive fluorescent dye in a highly plasticized polymer matrix. Furthermore, we have described a very simple method for preparing extremely small sensing devices for medical applications in a manner easy to fabricate.

Although the invention has been described and illustrated in detail, it is to be clearly understood that the same is by way of illustration and example only, and is not to be taken by way of limitation; the spirit and scope of this invention being limited only by the terms of the appended claims.

We claim:

1. A device for monitoring oxygen in an environmental in response to light transmitted from a light source comprising:
   an optical waveguide to receive light transmitted from the light source; and
   a coating of oxygen-sensitive medium disposed on said waveguide wherein said sensitive medium fluoresces in response to light from said light source, the intensity of fluorescence of said sensitive medium being dependent on the partial pressure of oxygen present in the environment being monitored, said sensitive-medium including an inorganic oxygen-sensitive fluorescent dye in a plasticized polymer matrix.

2. A device for monitoring oxygen as recited in claim 1, wherein: said plasticized polymer includes at least twenty-five percent plasticizer.

3. A device for monitoring oxygen as recited in claim 2, wherein:
   said oxygen-sensitive fluorescent dye includes tris (4,7-diphenyl-1,10-phenanthroline) Ru(II) perchlorate.

4. A device for monitoring oxygen as recited in claim 2, wherein:
   said oxygen-sensitive fluorescent dye is formed of any oxygen-responsive fluorescent salt of tris (4,7-diphenyl-1,10-phenanthroline) Ru(II) cation.

5. A device for monitoring oxygen as recited in claim 2, wherein:
   said oxygen-sensitive fluorescent dye is made of any oxygen-responsive, fluorescent salt of a transition metal complex having as a ligand a derivative of 1,10-phenanthroline.

6. A device for monitoring oxygen as recited in claim 2, wherein:
   said oxygen-sensitive fluorescent dye is made of any oxygen-responsive, fluorescent salt of a transition metal complex having as a ligand 1,10-phenanthroline.

7. A device for monitoring oxygen as recited in claim 5, wherein:
   said transition-metal complex is selected from the group consisting of ruthenium (II), osmium (II), rhodium (III) and iridium (III).

8. A device for monitoring oxygen as recited in claim 2, wherein:
   said plasticized polymer is formed of polyvinyl chloride plasticized with didecyl phthalate.

9. A device for monitoring oxygen as recited in claim 8, wherein:
   said plasticized polymer includes fifty weight percent of didecyl phthalate.

10. A device for monitoring oxygen as recited in claim 2, wherein:
    said plasticized polymer is plasticized with a derivative of phthalic acid, said derivative being compatible with said polymer.

11. A device for monitoring oxygen as recited in claim 2, wherein:
    said plasticized polymer includes a plasticizer selected from the group of materials consisting of phthalic acid derivatives, citric acid derivatives, adipic acid derivatives, and sebacic acid derivatives.

12. A device for monitoring oxygen as recited in claim 2, wherein:
    said plasticized polymer includes a polymer selected from the group of materials consisting of polyvinyl chloride, polystyrene, polyurethane, polyvinyl butyral, polymethyl methacrylate and silicone rubber.

13. A device for monitoring oxygen as recited in claim 1, wherein:
    said waveguide is a fiber optic waveguide having a core surrounded by a cladding, a portion of said cladding being removed from said waveguide to expose a portion of said core, said oxygen sensing medium being disposed on said exposed core.

14. A device for monitoring oxygen as recited in claim 1, wherein:
said waveguide is a fiber-optic waveguide having first and second ends, said oxygen-sensing medium being disposed on said first end of said waveguide, said light source being disposed at said second end of said waveguide.

15. A device for monitoring oxygen as recited in claim 1, wherein:
said waveguide is a fiber-optic waveguide having a core surrounded by a cladding and having first and second ends, said light source being disposed at said second end of said waveguide, said first end of said waveguide terminating in an acute angle exposing an elongated portion of said core, said oxygen sensing medium being disposed on said elongated portion of said core.

16. A device for monitoring oxygen as recited in claim 15, wherein:
said acute angle is less than about sixty degrees.

17. A device for monitoring oxygen as recited in claim 15, wherein:
said angle is between about twenty and about thirty degrees.

18. A device as recited in claim 1, further comprising:
a sleeve surrounding said waveguide, said sleeve being formed of a gas-permeable, solution-impermeable membrane.

19. A device for monitoring oxygen as comprising:
an acrylic optical fiber, having a generally cylindrical core surrounded by a cladding, said fiber having first and second ends, said first end terminating in an acute angle of between about twenty degrees and about thirty degrees to expose an elongated portion of said core; and
an oxygen-sensing medium composed of tris (4,7-diphenyl-1,10-phenanthroline) (RuII) perchlorate dye in a matrix of polyvinyl chloride and didecyl phthalate, said matrix consisting of fifty-weight-percent didecyl phthalate, said matrix being saturated with said dye, said oxygen sensing medium being disposed on said exposed portion of said core.

20. A device as recited in claim 19, further comprising:
a gas permeable, solution impermeable membrane disposed about said fiber and said sensing medium.

21. A method for forming an oxygen sensor comprising the steps of:
immersing an elongated portion of an exposed optical fiber core in an oxygen sensing medium dissolved in a volatile solvent, said solvent being unable to dissolve said fiber, and said elongated portion terminating in an acute angle of less than about sixty degrees; and
allowing said solvent to evaporate to cause said oxygen sensing medium to dry to a solid phase.

22. A method for forming an oxygen sensor as recited in claim 21 further comprising the step of:
forming a gas-permeable, solution-impermeable membrane about said fiber and said sensing medium.

23. A device for monitoring oxygen in an environment in response to light transmitted from a light source comprising:
a fiber-optic waveguide having a core surrounded by a cladding and having first and second ends, said light source being disposed at said second end of said waveguide, said first end of said waveguide terminating in an acute angle exposing an elongated portion of said core, said oxygen sensing medium being disposed on said elongated portion of said core.

24. A device for monitoring oxygen as recited in claim 23, wherein:
said acute angle is less than about sixty degrees.

25. A device for monitoring oxygen as recited in claim 23, wherein:
said angle is between about twenty degrees and about thirty degrees.

* * * * *